(12) United States Patent
Hardert et al.

(10) Patent No.: US 11,382,607 B2
(45) Date of Patent: Jul. 12, 2022

(54) ROTATING FULL-CORE BIOPSY NEEDLE

(71) Applicant: Cook Medical Technologies LLC, Bloomington, IN (US)

(72) Inventors: Michael W. Hardert, Bloomington, IN (US); Thomas W. McGhie, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 202 days.

(21) Appl. No.: 15/583,133

(22) Filed: May 1, 2017

(65) Prior Publication Data
US 2017/0325792 A1 Nov. 16, 2017

Related U.S. Application Data

(60) Continuation of application No. 14/874,863, filed on Oct. 5, 2015, now Pat. No. 9,763,649, which is a division of application No. 13/740,312, filed on Jan. 14, 2013, now Pat. No. 9,149,293, which is a continuation of application No. PCT/US2011/045266, filed on Jul. 26, 2011.

(60) Provisional application No. 61/369,119, filed on Jul. 30, 2010.

(51) Int. Cl.
 *A61B 10/02* (2006.01)
 *A61B 17/34* (2006.01)
 *A61B 17/32* (2006.01)

(52) U.S. Cl.
 CPC ...... *A61B 10/0275* (2013.01); *A61B 10/0266* (2013.01); *A61B 17/3417* (2013.01); *A61B 2017/320064* (2013.01)

(58) Field of Classification Search
 CPC ........... A61B 10/0275; A61B 10/0266; A61B 17/3417
 USPC .......................................................... 600/567
 See application file for complete search history.

(56) References Cited

U.S. PATENT DOCUMENTS

| | | | |
|---|---|---|---|
| 4,873,991 A | 10/1989 | Skinner | |
| 5,573,008 A | 11/1996 | Robinson et al. | |
| 5,800,389 A * | 9/1998 | Burney | A61B 10/0233 604/158 |
| 6,764,452 B1 | 7/2004 | Gillespie et al. | |
| 8,187,203 B2 | 5/2012 | McClellan | |
| 9,072,506 B1 * | 7/2015 | Seiger | A61B 10/0275 |
| 2007/0123798 A1 | 5/2007 | Rahamimov | |
| 2007/0123800 A1 | 5/2007 | Nishtala et al. | |
| 2007/0213633 A1 | 9/2007 | McClellan | |

(Continued)

FOREIGN PATENT DOCUMENTS

| WO | WO 1999/34734 A1 | 7/1999 |
|---|---|---|
| WO | WO 2005/013831 A2 | 2/2005 |
| WO | WO 2006/081556 A2 | 8/2006 |

*Primary Examiner* — Daniel L Cerioni
(74) *Attorney, Agent, or Firm* — Woodard, Emhardt, Henry, Reeves and Wagner LLP

(57) ABSTRACT

There is disclosed, among other things, embodiments of a biopsy needle for taking a full core sample through soft tissue. In the illustrated embodiments, the needle includes a single monolithic tubular member having a notch cut partway through a distal portion of the tubular member to form an arch-shaped finger. At least a portion of the finger is bent toward the notch and into the lumen of the tubular member. Methods for using these embodiments are also described.

20 Claims, 5 Drawing Sheets

(56) References Cited

U.S. PATENT DOCUMENTS

2010/0305519 A1\* 12/2010 McKinnon ........ A61M 25/0105
    604/272
2013/0041286 A1   2/2013 Theobald et al.

\* cited by examiner

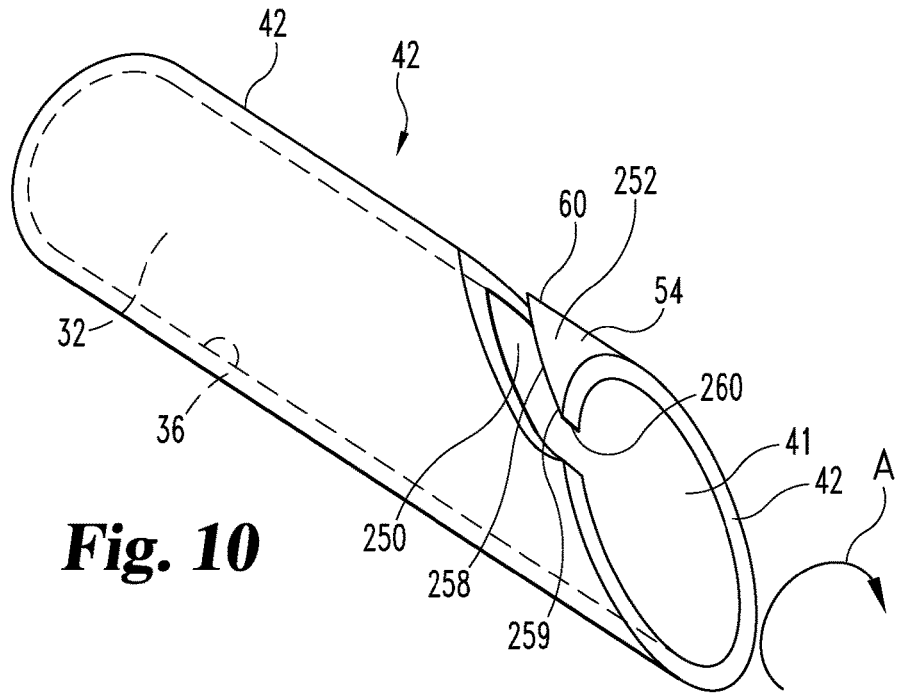
Fig. 10
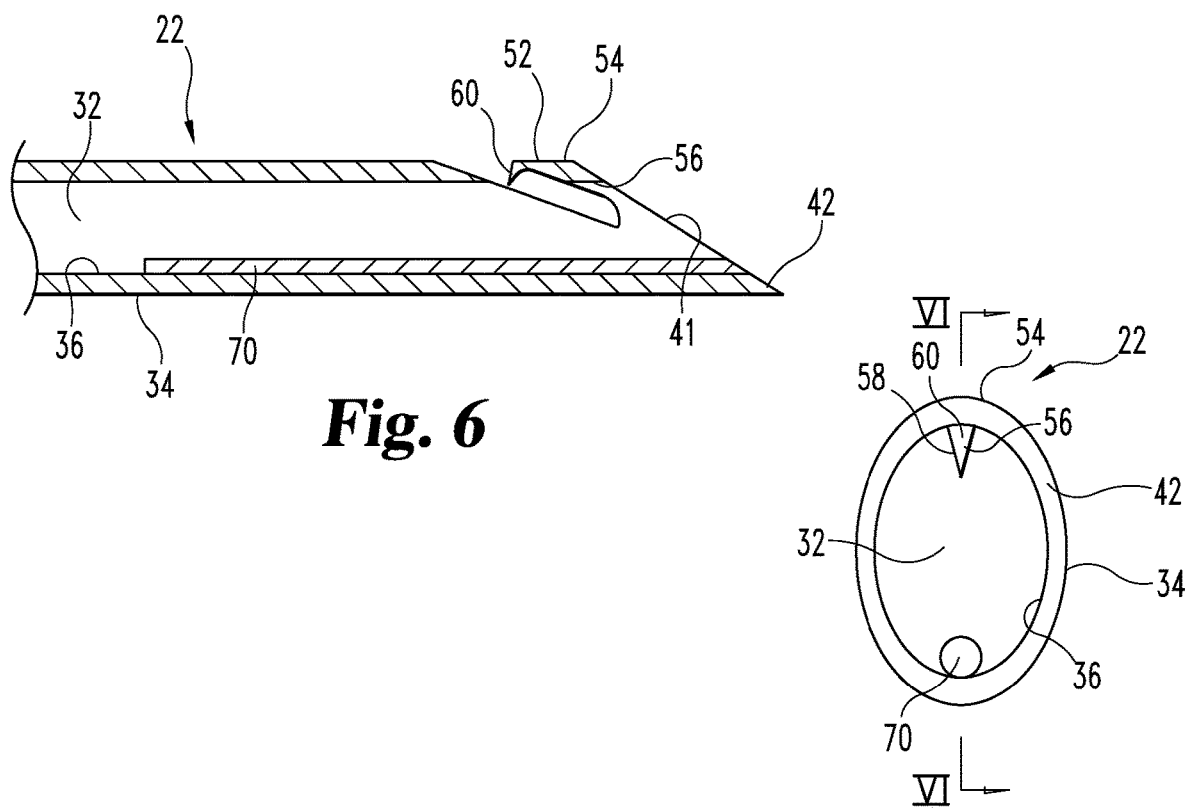
Fig. 6
Fig. 5

ROTATING FULL-CORE BIOPSY NEEDLE

STATEMENT OF RELATED APPLICATIONS

This application is a continuation of Ser. No. 14/874,863, filed Oct. 5, 2015 which is a divisional of Ser. No. 13/740,312, filed Jan. 14, 2013, which is a continuation of PCT/US2011/045266, filed Jul. 26, 2011, which claims the benefit of priority of U.S. Provisional Patent Application Ser. No. 61/369,119 filed Jul. 30, 2010, each of which is incorporated herein by reference in its entirety.

The present disclosure concerns devices and methods for procuring samples of living tissue for assay, study or other diagnostic or therapeutic purposes.

BACKGROUND

There are a number of tools, devices and methods that have been used to obtain a sample of tissue from a patient, for testing and diagnosis of potential medical problems with the specific tissue or the patient in general. Attempts have been made to make the procedure as minimally-invasive as possible. To that end, needles have been developed which can be inserted through the skin of a patient directly or through the vasculature to a tissue mass or other particular location from which a sample is desired. Through mechanical or other means a sample is captured by the needle, and the needle is withdrawn with the sample.

Several difficulties with this type of needle have been noted over time. Many have utilized inner and outer cannulas that slide with respect to each other. Such devices make an opening through the patient of the outer diameter of the outermost cannula, while only obtaining a sample that is at most the width of the inner diameter of the innermost cannula. Thus, the opening that must be made in the patient is generally significantly larger than the size of the tissue sample, or conversely, for a desired amount of tissue, the opening to be made in the patient must be larger and consequently more uncomfortable. Similarly, some existing needles have suffered from difficulties in controlling or maintaining the tissue sample until it can be transferred to storage or analysis areas. Withdrawal of the needle can leave the tissue behind within the patient, particularly if the tissue must be pulled away from other tissue joined across its width.

Accordingly, there remains a need for a biopsy needle that is capable of obtaining a sample of a desired size while keeping the profile of the opening in the patient minimal, and/or is effective in maintaining the sample while allowing it to be easily removed from the needle into a storage or testing device.

SUMMARY

Among other things, there is disclosed a biopsy needle having an elongated tubular member adapted for insertion through tissue to move tissue into the member. The tubular member has a longitudinal axis, an outer surface, and an inner surface defining a lumen along the axis. The member has a distal insertion portion with a distal end surface that is oblique to the axis. The distal insertion portion includes a notch through a portion of the outer and inner surfaces and into the lumen and directed generally toward the axis. The distal insertion portion thus includes a generally arch-shaped finger distal of the notch, which includes at least part of the distal end surface. At least a portion of the finger adjacent the notch is bent with respect to the rest of the tubular member into the lumen, so that that portion of the finger within the lumen is adapted to contact and compress tissue as tissue moves through the lumen. The tubular member is adapted so that its outer surface contacts tissue when the tubular member is inserted through tissue to move tissue into the member.

In other embodiments, the bent portion forms a sharpened tooth adapted to cut a profile in tissue when tissue is within the lumen and the tubular member is rotated around its longitudinal axis. The tubular member may be monolithic. The finger can connect to the rest of the tubular member at two locations, so that the finger has two end portions that are not detached from the tubular member. Alternatively, the finger has first and second end portions, and the first end portion is disconnected from the rest of the tubular member. In that case, the first end portion can form some or all of a bent portion of the finger. A key can be formed along a portion of the inner surface of the tubular member. The tubular member may include a slot through the inner and outer surfaces that is adapted to permit a tissue sample to exit the tubular member, and the slot may be proximal of the notch.

The needle can be made a part of a biopsy needle system. For example, such a system in particular embodiments includes a mandrel insertable into the needle's lumen through its end surface. The mandrel is configured to slide into and out of the lumen without interfering with a bent portion of the finger. The mandrel may be configured with a first portion shaped substantially identically to the inner surface of the tubular member of the needle, and a second portion including a groove or flat surface for accommodating passage of a bent portion of the finger.

In other embodiments, a biopsy needle includes an elongated tubular member adapted for insertion into a patient to obtain a tissue sample, having a proximal portion, a distal portion having a distal end, and a central longitudinal lumen along a longitudinal axis from the proximal portion through the distal portion and the distal end. The distal end includes a finger separated from the rest of the tubular member by a notch, a portion of the finger being bent toward the notch so that a portion of the finger extends into the lumen. When a tissue sample enters the lumen it contacts that portion of the finger and extends beyond the finger within the lumen. The tubular member is configured so that rotation around the axis causes at least a portion of tissue within the lumen to be separated from adjacent tissue.

Particular embodiments include those in which the finger is adapted to elastically flex outward away from the lumen by pressure from a tissue sample moving through the lumen when the tubular member is forced through tissue. The portion of the finger extending into the lumen may include at least one tooth having a sharp edge. For example, where the tubular member has a leading edge, the tooth and sharp edge may be in a portion of the tubular member diametrically opposite to the leading edge, or lateral of the leading edge. The notch can extend through a distal-facing surface in the distal end of the tubular member at a first location, with the tooth being a portion of the finger adjacent that first location. A longitudinal protrusion may be fixed to the tubular member within the lumen, e.g. such that the protrusion substantially faces the notch. A mandrel can be provided having a first portion movable through the lumen, with that first portion having a surface configured to face the tooth in the tubular member so that the mandrel can move without substantial interference with the tooth. Such a mandrel could include a surface that is at least one of flat and longitudinally grooved.

Methods for making and using biopsy needles are also disclosed. For example, a method of taking a biopsy in particular embodiments includes providing a needle having a tubular member with a notch defining a distal finger and a lumen, a portion of the finger being bent with respect to the rest of the tubular member into the lumen. The tubular member is inserted into tissue of a patient that is to be sampled, so that tissue to be sampled enters the lumen to a position proximal of the finger. The needle is rotated with respect to the tissue, so as to reduce the area of connection between the tissue within the lumen and adjoining tissue. The needle is withdrawn from the patient, with a portion of the finger bent into the lumen blocking the tissue proximal of the finger and within the lumen from exiting the needle. As particular examples, the rotating can cause a portion of the finger to cut a profile through tissue within the lumen, or the rotating can generate twisting strain between tissue within the lumen and adjoining tissue. Separation between tissue within the lumen and adjoining tissue, or weakening of the join between tissue within the lumen and adjoining tissue, results.

These and other embodiments of structure and methodology are given in the following disclosure.

BRIEF DESCRIPTION OF THE DRAWINGS

FIG. 5 is an end view of the embodiment of either FIG. 1 or FIG. 8 with additional structure.

FIG. 6 is a cross-sectional view taken along the line VI-VI in FIG. 5 and viewed in the direction of the arrows.

FIG. 10 is a perspective view of a portion of an embodiment of a biopsy needle according to this disclosure.

DESCRIPTION OF THE ILLUSTRATED EMBODIMENTS

Figure 1:
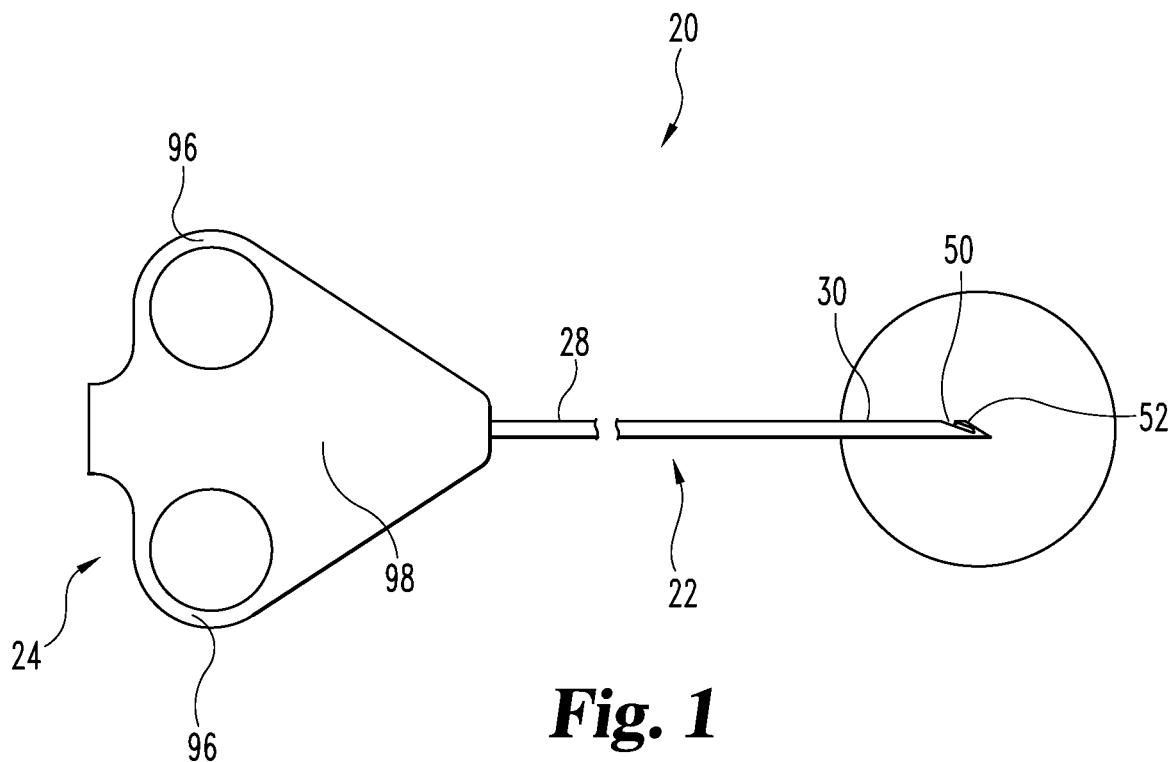
FIG. 1 is a side plan view of an embodiment of a biopsy needle according to this disclosure.

Reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates.

Referring now generally to the figures, there is shown a biopsy needle 20 generally in the form of an elongate tubular member 22. A handle or grip 24 may be provided in some embodiments to assist the user in gripping and manipulating member 22. As discussed further below, in embodiments having a handle 24, member 22 is connected (e.g. mechanically) to handle 24, and may be fixed or rotatable with respect to handle 24.

Tubular member 22 is in the form of a hollow cannula or needle in the illustrated embodiment, and includes a proximal portion 28 toward the user and a distal portion 30 that extends away from the user and is adapted for insertion within the patient to a location from which a tissue sample is desired. If present, handle or grip 24 is attached to proximal portion 28, in one example at the end of proximal portion 28. Proximal portion 28 and distal portion 30 are part of the same cylindrical tube in a particular embodiment, which may be circular, oval or otherwise cross-sectionally shaped and which includes a central lumen 32 that extends along the longitudinal axis of member 22 through the whole length of member 22. In other embodiments, lumen 32 may extend within distal portion 30 a length sufficient to obtain a desired core of tissue, or may extend into but not all the way through proximal portion 28.

Distal portion 30 has the same general external and internal profile as proximal portion 28, except as noted below. An external cylindrical surface or wall 34 is continuous along proximal portion 28 and most of distal portion 30. Likewise, an internal cylindrical surface or wall 36 surrounds lumen 32 through any part of proximal portion 28 that lumen 32 extends, and surrounds lumen 32 through most of distal portion 30. The illustrated embodiment shows lumen 32 and wall 36 as having a circular cross section, and wall 34 as having a concentric circular cross section. It will be understood that the shape or profile of walls 34 and 36 may differ from one another, may be non-uniform in whole or part, or may be non-concentric in other embodiments.

Figure 3:
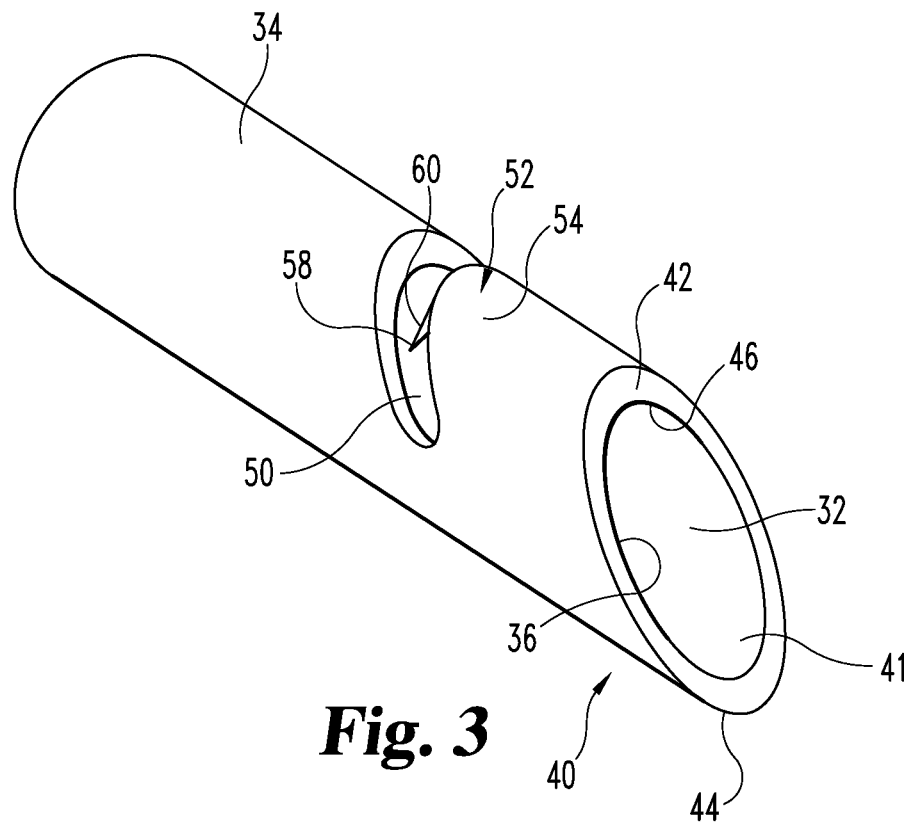
FIG. 3 is a perspective view of the portion shown in FIG. 2.
Figure 4:
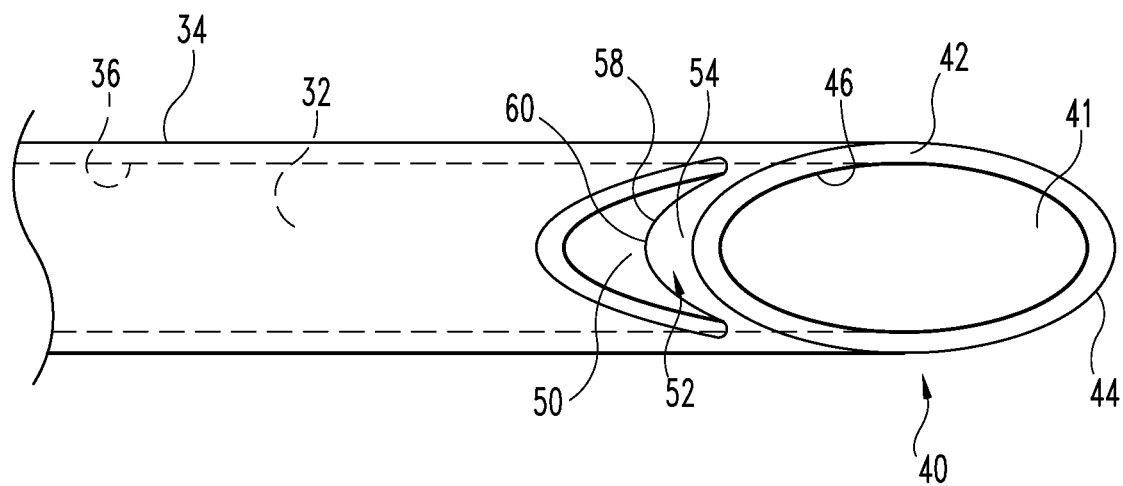
FIG. 4 is a top view of the portion shown in FIG. 2.

Distal portion 30 has an end 40 through which lumen 32 exits at opening 41. End 40 is sharpened so as to ease the entry and movement of member 22 into and through the patient's tissue. In the illustrated embodiment, end 40 has an end surface 42 that is oblique with respect to the longitudinal axis of member 22. Surface 42 extends between walls 34 and 36, and thus has a width generally similar or identical to the thickness of the wall of member 22 (i.e. the thickness between surfaces 34 and 36). Distal edge 44 is the intersection of surface 42 and wall 34 furthest from the user, and an edge 46 is formed at the intersection of surface 42 and wall 36. Surface 42 and edges 44 and 46 are formed in a particular embodiment by cutting a cylindrical tube obliquely, with a sharper angle of cut providing thinner or sharper edges 44 and 46. Some or all of edges 44 and/or 46 may be further honed or sharpened, for example at least along their leading or most-distal portions (e.g., for edge 46, along an upper portion of wall 36 as seen in FIGS. 3-4), as by sandpaper or other grinding or roughened surfaces in particular embodiments. As will be further discussed below, as member 22 is inserted through tissue, edges 44 and 46 cut a profile so that tissue separates, with a sample entering lumen 32 and surrounding tissue contacting external surface 34.

Distal portion 30 further has a notch 50 through surfaces 34 and 36 and into lumen 32, creating a finger 52. In the illustrated embodiment, notch 50 is substantially planar and oblique with respect to the longitudinal axis of member 22. In the particular illustrated embodiment, notch 50 is angled less steeply with respect to the longitudinal axis of member 22 than is surface 42. That is, surface 42 is closer to perpendicular with respect to the longitudinal axis than notch 50, and notch 50 is closer to parallel with respect to the longitudinal axis than is surface 42. In such embodiments, finger 52 extends further longitudinally at one portion (the entry of notch 50 into tubular member 22, or the top or the portion opposite the leading edge of tubular member 22 as viewed in FIG. 2) than it does at other portions, such as those adjacent the end of notch 50. In other embodiments, notch 50 may be substantially parallel to the front surface 42 of member 22, or otherwise oriented. The illustrated embodiment shows notch 50 extending about half-way through tubular member 22 and having a width of about 0.5 to 1.5 mm or less, for example about 1 mm. Such a small notch width compared to the overall length of tubular member 22 (e.g. 20-200 mm) allows the configurations described herein, while minimizing or preventing tissue from entering or exiting tubular member 22 through notch 50.

With the exception of notch 50, exterior surface 34 is substantially uniform from proximal portion 28 through distal portion 30 to edge 44. Finger 52 is contiguous with the rest of tubular member 22, and in this embodiment forms essentially an arch with an outer surface 54 and an inner surface 56, which (in the view of FIG. 1) are at least partially congruent with surfaces 34 and 36. By "congruent," it is meant that surface 54 is part of the same geometric cylinder as wall surface 34 and surface 56 is part of the same geometric cylinder as wall surface 36, which naturally follows from the monolithic nature of tubular member 22 in the illustrated embodiments. As with edges 44 and 46, notch 50 creates an edge 58 of finger 52 that faces notch 50 which is thin or sharp due to the oblique angle of notch 50 with respect to the longitudinal axis, and edge 58 may be further honed or sharpened. The amount of material in finger 52 is minimized in the illustrated embodiment, as for example to a finger width of about 0.5 mm to 1.5 mm or less, such as about 1 mm.

In the illustrated embodiments, at least a portion of finger 52 is bent proximally, i.e. into notch 50, so that a portion or tooth 60 of finger 52 enters at least minimally into lumen 32 of tubular member 22 at a point proximal of surface 42. The illustrated embodiment shows a tip portion of finger 52 bend down into notch 50 to form at least one tooth 60, which includes at least part of edge 58. The illustrated embodiment shows only one tooth 60 which holds and/or cuts tissue within tubular member 22, as will be discussed further below, but multiple teeth 60 can be provided in other embodiments. At least part of tooth 60 and edge 58 are inside the extent of internal wall surface 34, i.e., the distance from the central (longitudinal) axis to edge 58 is less than the distance from that axis to surface 34. While the illustrated embodiment shows only a portion of finger 52 bent into notch 50, it will be understood that more or all of finger 52 may be bent or pivoted, for example so that surface 42 is in essentially two planes that intersect at an axis at which finger 52 is bent.

Figure 2:
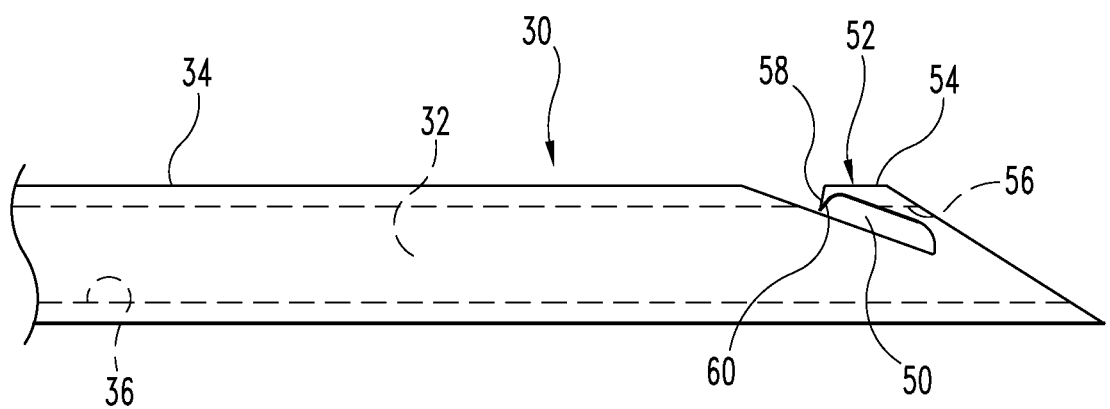
FIG. 2 is a close-up side view of a portion of the embodiment shown in FIG. 1.

In particular embodiments, finger 52 and tooth 60 have a static (e.g. unstressed) configuration as in FIG. 2, with one or both adapted to allow elastic bending from that static configuration further into or out of notch 50. In other embodiments, the static configuration of finger 52 and tooth 60 seen in FIG. 2 does not permit significant (or any) bending by forces from tissue encountered during use. Notch 50 may be formed by mechanical cutting or grinding, laser cutting or other processes. Tooth 60 or other bent portion(s) of finger 52 are bent or formed in a configuration similar to FIG. 2 during the manufacturing process in certain embodiments, so as to make needle 20 ready-to-use for the physician or other medical professional. The noted configuration may be created at some other point prior to usage in other embodiments, or the configuration may be established as a part of the preparation of device 20 for use or during use.

Illustrated embodiments (e.g. FIGS. 2-4) show notch 50 as substantially linear or planar. Other embodiments of a notch may have a different configuration or shape, e.g. non-linear, curvate, having sides that are arcuate and/or non-parallel, or the like. For example, embodiments may have a notch 50 with a curve rather than being substantially linear or planar. In such embodiments, from tooth 60, edge 58 curves around tubular member generally toward distal end surface 42 (e.g. FIGS. 5-6, in which edge 58 has a slightly convex form viewed from the side, rather than a straight form). In that configuration, the material of tubular member 22 forming finger 52 is narrowed or minimized in size along the longitudinal dimension, making bending of finger 52 somewhat easier at any of a number of locations. Such a configuration of notch 50 and finger 52 may allow more of finger 52 to be easily placed in the bent configuration, and/or a larger portion of finger 52 to be bent into one or more teeth 60, so that more of tooth 60 (and finger 52) extends into lumen 34.

Referring now to FIGS. 5-6, embodiments of tubular member 22 may include structure for gripping or holding tissue within lumen 32. In the illustrated embodiment, an elongated ridge or spline 70 forming essentially a parallel key is shown. Ridge 70 is shown as a rounded or roughly circular element attached to inner wall 36, so that ridge 70 and wall 36 are approximately tangent to each other. Ridge 70 may have other cross-sectional shapes or configurations, including non-uniform shapes or configurations, that can hold or grip tissue. For example, ridge 70 may have one or more flat surfaces, such as a rectangular, square, triangular or other regular or irregular polygonal shape in cross-section. As another example, a rounded ridge 70 (such as that in FIG. 5) may be affixed to inner wall 36 by a linear or rounded flange or leg. Ridge 70 extends from the end surface 42 of tubular member 22 proximally toward or into proximal portion 28 of member 22 in the illustrated embodiment. In other embodiments, ridge 70 ends interior or surface 42, i.e., ridge 70 does not extend all the way to surface 42. The distal-most portion of ridge 70 may be beveled (e.g. parallel to surface 42) or present a leading edge so as to reduce resistance to the movement of ridge 70 through tissue. In this embodiment, ridge 70 is placed and oriented to contact tissue within lumen 32 so that such tissue cannot rotate significantly with respect to tubular member 22. As shown, that orientation can be parallel to the longitudinal axis of tubular member 22, as well as other orientations.

Figure 7:
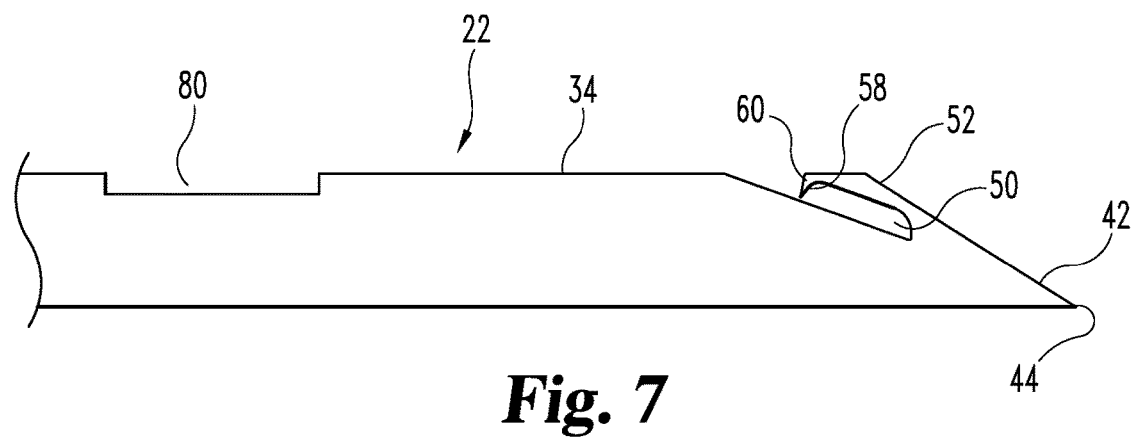
FIG. 7 is a side plan view of a portion of a biopsy needle embodiment.
Figure 8:
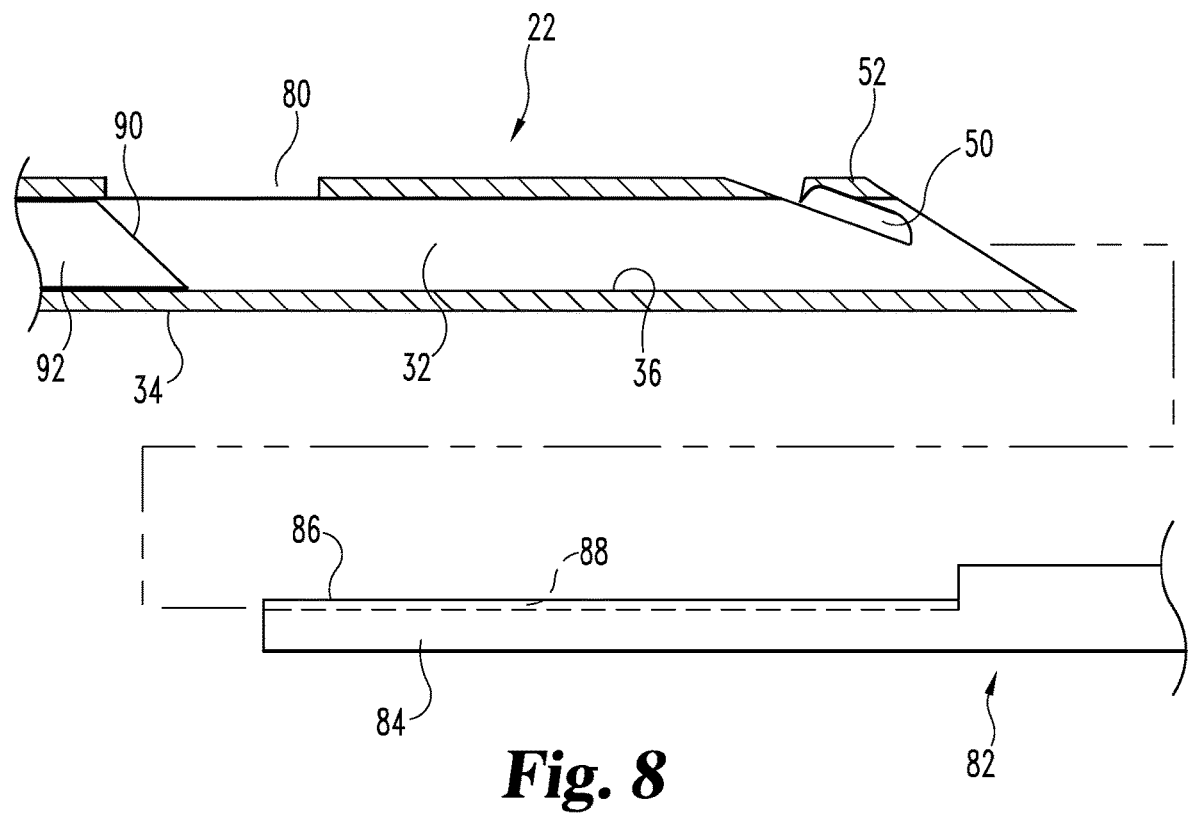
FIG. 8 is a side, part cross-sectional view of the embodiment of FIG. 7 with additional structure.

Referring now to FIGS. 7-8, there is shown an embodiment of tubular member 22 that includes a slot 80 through surfaces 34 and 36. In the illustrated embodiment, slot 80 opens through a portion of tubular member 22 that is linearly proximal of notch 50, i.e. rearward along a path parallel to the longitudinal axis of tubular member 22. In other words, if notch 50 is considered to be in a "top" portion of member 22, slot 80 is also in a "top" portion of member 22, merely proximal of notch 50. Slot 80 may be used, among other things, for easy removal of a tissue sample from lumen 32. For that purpose, a mandrel 82 may be provided to push tissue in a proximal direction toward and/or out of slot 80. Mandrel 82 is generally an elongated member generally of the shape and approximate size of lumen 32, having an end portion 84 with a reduced cross-section, groove or keyway to accommodate finger 52 and/or its tooth 60. For example, end portion 84 may have a lower part-circular cross-section with an upper flat surface 86. Instead of or in addition to surface 86, a circular, rectangular or other groove or keyway 88 (FIG. 8) can be provided in end portion 84 to allow end portion 84 to move past tooth 60 and any other portion of finger 52 in lumen 32 without interference. Of course, in embodiments in which ridge 70 is provided in tubular member 22, a flattened surface, groove or keyway or similar opening to accommodate ridge 70 is provided in mandrel 82, so that mandrel 82 can easily slid within lumen 32. A ramp 90 may be inserted through proximal portion 28 (as on the end of a stylet 92) or into the proximal portion of slot 80 to act as an inclined plane directing tissue out of slot 80 when tissue is pushed by mandrel 82.

Handle 24 in the illustrated embodiment has two rounded finger-holds or grips 96 and a central body 98 attached to tubular member 22. This embodiment does not require springs, triggers, or other mechanical devices to propel tubular member 22 forward with respect to handle 24. However, if needle 20 or tubular member 22 are used with additional structure, a handle having such propulsion devices may be used. Further, it will be seen that a handle need not have the holds or grips 96 in some embodiments, and may include simply a body attached to proximal portion 28 of tubular member 22, e.g. in the form of a textured knob or similar structure.

Use of needle 20 to obtain a sample of soft tissue, e.g. of a subcutaneous lump or cyst, will now be described. It will be understood that other uses of needle 20 may be made, such as into an organ (e.g. the liver via routes such as the hepatic vein) or other tissues subcutaneously or through the vasculature.

Figure 9A:
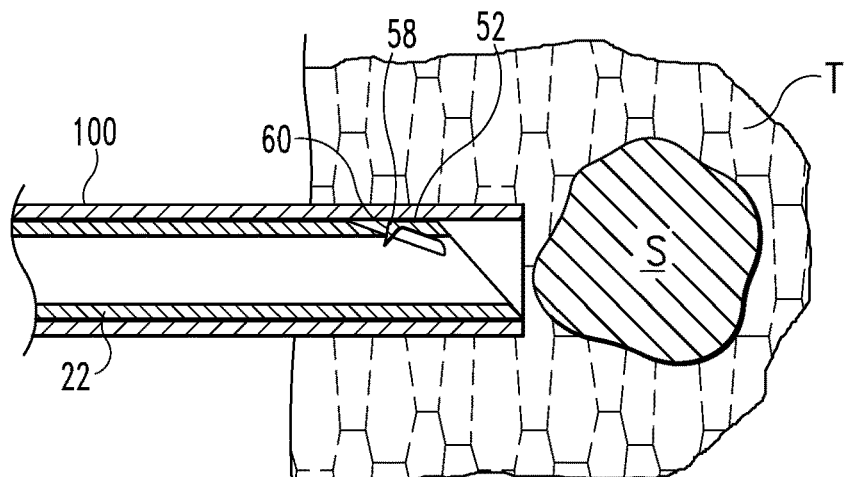
FIGS. 9A-9C are cross-sectional views of an embodiment showing insertion and use of biopsy needle embodiments of the disclosure.

In many cases, the physician or other medical professional will begin the procedure by inserting an introducer needle 100 (e.g. FIG. 9A) into tissue T of a patient so that the distal end of the introducer needle is in or adjacent to the tissue of interest to be sampled (e.g. a lump) S. In such cases, the user will find an appropriate point on the skin of the patient that is proximate to the tissue to be sampled, preferably one such that the introducer needle can be inserted straight to the tissue to be sampled without curving and with little or no impact or damage to vital vessels, nerves, organs or other important tissues between the skin and the tissue to be sampled. With such an introducer needle 100 in place, tubular member 22 of needle 20 can be inserted through the introducer needle to the tissue to be sampled. If such an introducer needle is not used, tubular member 22 of needle 20 can be inserted directly through the skin and other tissue to the tissue to be sampled. In the latter case, to avoid undesired tissue entering lumen 32, a mandrel (e.g. mandrel 82) is inserted through lumen 32 so that the opening of lumen 32 through surface 42 is substantially blocked. When needle 20 is in or adjacent the tissue to be sampled, mandrel 82 is withdrawn (e.g. through proximal portion 28), leaving lumen 32 open.

Figure 9B:
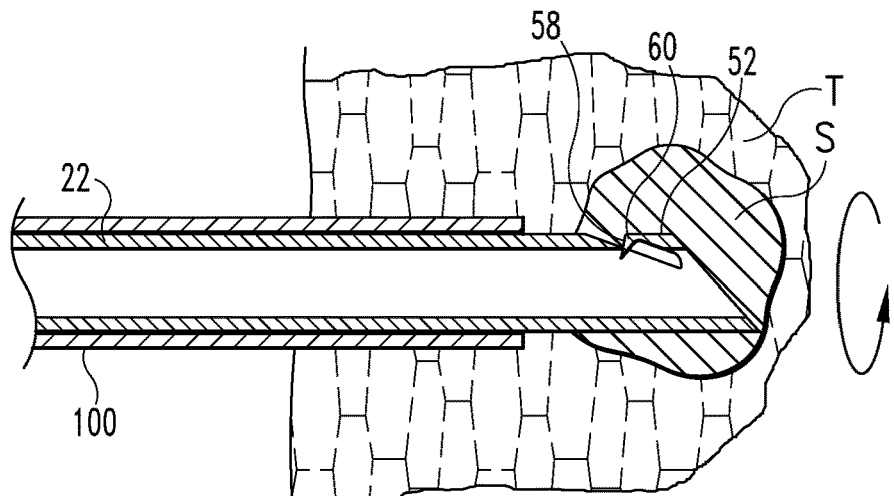

The user then moves tubular member 22 forward through the tissue (e.g. out from the introducer needle, if used) a desired distance as indicated in FIG. 9B. For example, the user may advance tubular member 22 so that surface 42 is at or just beyond the end of the lump or other tissue of interest S for biopsy, so as to obtain the greatest possible amount of core for analysis. As tubular member 22 moves forward, it cuts a profile through the tissue (e.g. led by edges 44 and 46), so that outside surface 34 contacts and moves along tissue and a column or core of tissue enters lumen 32, within or in contact with inner surface 36. As noted above, in particular embodiments notch 50 is narrow and does not present a sharpened edge directed toward tissue so that little or no tissue enters lumen 32 through notch 50. If ridge 70 is provided, tissue entering lumen 32 is separated by or moves over and around ridge 70, so that ridge 70 engages the tissue along one or more surfaces.

As tissue enters lumen 32, within wall 36, the tissue comes into contact with at least part of tooth 60 of finger 52, particularly its inner surface 56. In embodiments in which tooth 60 and/or other parts of finger 52 are elastically outwardly bendable, the tissue tends to push outward and bend tooth 60 and/or finger 52 outward. Tooth 60 and/or finger 52 react by exerting an inward pressure on or forcing its way into the tissue sample, due to its elasticity. In embodiments in which finger 52 is not outwardly bendable by the bulk of the tissue sample, the tissue sample is compressed by tooth 60 and/or finger 52 as it passes. As portions of the tissue sample contact the portion of inner surface 56 of tooth 60, surface 56 exerts inward pressure on the tissue sample. When past tooth 60, such compression the sample experiences from tooth 60 and/or finger 52 is released, reducing stress on the tissue sample and allowing it to resume or approach its original diameter, e.g. expand toward inner surface 36 of lumen 32.

As noted, needle 20 is advanced through the tissue mass from which a sample is desired so that a core of the tissue mass is within lumen 32. That is, the advancement of needle 20 should stop when most or all of the desired tissue core is past surface 42 or tooth 60. When so positioned, tubular member 22 is rotated about its longitudinal axis (as indicated in FIG. 9B). In embodiments in which a handle (e.g. handle 24) is present and tubular member 22 is rotatable with respect to handle 24, the user holds handle 24 and rotates tubular member 22. If tubular member 22 and handle 24 are fixed with respect to each other, the user rotates handle 24, which turns tubular member 22 around its axis. If tubular member 22 and handle 24 are not fixed with respect to each other, a grip or knob connected to tubular member 22 (not shown) may be rotated with respect to handle 24 in order to rotate tubular member 22. In embodiments in which needle 20 is inserted through an introducer needle 100 in the patient, the introducer needle 100 can act as a guide to help control rotation of needle 20.

Rotating tubular member 22 around its axis assists in separating the tissue sample within lumen 32 from tissue to which it remains attached. In embodiments without ridge 70, turning tubular member 22 rotates edge 58 of tooth 60 with respect to the tissue. Edge 58 (and/or other aspects of tooth 60 or finger 52) cuts a profile through part or all of the thickness of the tissue sample, generally toward the longitudinal axis of tubular member 22. The profile eliminates or reduces the area of connection between the tissue sample in lumen 32 and adjacent tissue, thus reducing or eliminating the force required to pull the tissue sample away from adjacent tissue. In embodiments in which ridge 70 is present, or in which tooth 60 or other part of finger 52 presses the tissue sample against surface 36 enough to hold the tissue against rotation with respect to tubular member 22, turning tubular member 22 causes ridge 70 and/or tooth 60 (or finger 52) to push against and turn the tissue sample, creating a twisting strain between the sample and the tissue it remains connected to. Application of such a strain results in the shearing of the sample away from adjacent tissue, so that the sample is separated and can be pulled out. In embodiments in which ridge 70 is present, tooth 60 or edge 58 may not necessarily cut a substantial profile insofar as the tissue substantially moves with tooth 60, or may only pierce the tissue sample, and tooth 60 acts to hold and compress the tissue within lumen 32.

Figure 9C:
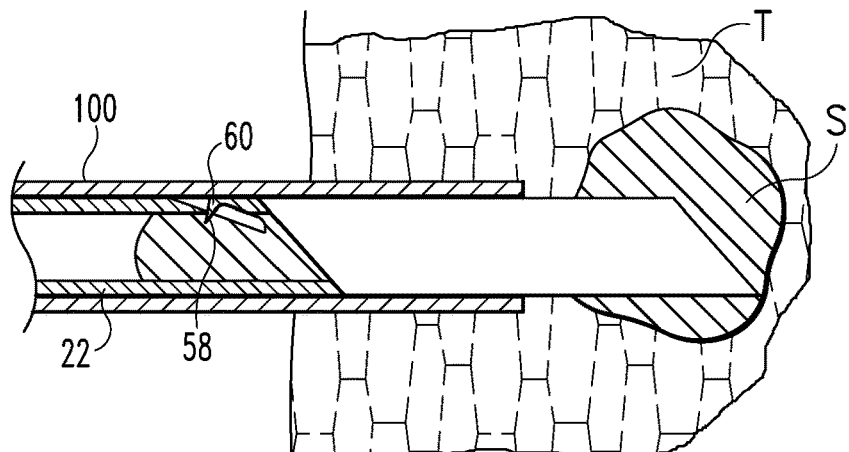

Having rotated tubular member 22 around its longitudinal axis and reduced or eliminated the connection with adjacent tissue (e.g. by twisting strain and/or by cutting tissue), and thus reduced or eliminate the force needed to separate the sample from adjacent tissue, needle 20 is withdrawn from the patient (e.g. FIG. 9C). The user pulls tubular member 22

(as by handle 24, if present) backwards so that tubular member 22 travels out of the patient along its insertion route. The illustrated embodiments of tubular member have a smooth exterior wall 34 (including a smooth outer surface 54 of tooth 60), with no part extending outside of wall 34, so that withdrawal of needle 20 has little risk of scoring or damage to surrounding tissue by extending matter. Tissue outside tubular member 22 that travels along notch 50 as needle 20 is withdrawn does not enter notch 50, or if slightly within the boundary of external surface 34, can be smoothly forced out with little or no damage by the exterior surface 54 of tooth 60 and/or finger 52.

Tooth 60 further operates as a barrier or grip to pull the tissue sample free (if necessary) and to prevent it from escaping from lumen 32 during withdrawal. With a portion of tooth 60 within lumen 32 and the tissue sample past tooth 60 and occupying substantially all of lumen 32, force (whether pulling from adjacent tissue on the sample, gravity on the sample, or another force) tending to move the sample out of the distal end of needle 20 is countered by the obstruction of tooth 60 and/or finger 52. For example, if there remains some connection between the tissue sample and adjacent tissue, the adjacent tissue will pull on the tissue sample as needle 20 is withdrawn. The pulled sample abuts tooth 60 (e.g. outer surface 54), and tooth 60 counters that pulling force, resulting in separation of the sample from the adjacent tissue. In embodiments in which tooth 60 is bendable with respect to the rest of tubular member 22, pulling the tissue sample against surface 54 of tooth 60 may result in bending of tooth 60 and/or finger 52 further into notch 50 and/or lumen 32, increasing the level of obstruction and counter-force by tooth 60 and/or finger 52 to prevent loss of the tissue sample. Once the sample tissue is fully separated from adjacent tissue, tooth 60 faces or abuts the sample, blocking or interfering with any tendency of the tissue to travel toward the distal end and fall out of tubular member 22.

With needle 20 removed from the patient, the tissue sample is removed from tubular member 22. In some embodiments, finger 52 can be moved out of the way of the tissue sample, and a stylet or mandrel (e.g. mandrel 82 noted above, or a fully-cylindrical stylet) can be inserted through the proximal portion 28 to push the tissue sample out of the distal portion 30 of tubular member 22. In embodiments noted above that have slot 80, stylet 92 can be inserted through proximal portion 28 of tubular member 22 so that its ramp 90 is opposite at least a portion of slot 80. Mandrel 82 is inserted into distal end 30 of member 22 so that its flat surface 86 (and/or groove or keyway 88 noted above) faces finger 52. Mandrel 82 is moved along tubular member 22, to contact and push the tissue sample against ramp 90, which directs it out of slot 80. The sample is placed in an appropriate receptacle from slot 80 for storage or analysis.

Needle 20 is constructed from materials generally known in the art. For example, handle 24 may be made principally of hard plastics or other suitable sturdy materials. Tubular member 22 may be made principally of biocompatible metals (e.g. stainless steel or titanium), with a wall made as thin as possible without sacrificing the rigidity and sturdiness needed for insertion through the patient's tissues without crushing or otherwise damaging member 22. Notch 50 may be made by grinding, laser cutting or other form of precision material removal. The inner diameter (e.g. diameter of wall 36) is made large enough to obtain the necessary sample without significant or substantial physical damage to the tissue. Compared to needles that use inner and outer tube components that slide with respect to each other, the single-tube construct of needle 20 allows a larger inner diameter, and thus a larger tissue sample, for a given outer diameter. Conversely, needle 20 permits a smaller outer diameter, and thus a potentially less-invasive, less-painful and easier-to-heal biopsy, for a given diameter of tissue sample.

In the embodiment of FIG. 2, notch 50 is cut or formed so that finger 52 is essentially a complete arch fixed at both ends. That is, finger 52 is connected to the rest of member 22 at both ends of finger 52, and is continuous between those ends and from those ends into the rest of member 22. An embodiment shown in FIG. 10 includes finger 252 being separated on one side from the rest of tubular member 22. Notch 250 is cut or formed so that one side extends through surface 42, creating an end of arch-shaped finger 252 that is not connected to the rest of tubular member 22. That separated portion 259 of finger 52 is bent inward, into lumen 32, to form a tooth 260. In that embodiment, finger 52 (and portion 259 and tooth 260) is not substantially bendable by tissue moving through.

Tooth 260 acts like tooth 60 to allow tissue past within lumen 32, and to cut, weaken and/or pull tissue beyond tooth 260 away from adjacent tissue. It has been found that this embodiment moves into test material more easily if needle 20 is rotated as it is inserted into the sample. Such rotation is around the longitudinal axis of tubular member 22, and in a direction not led by tooth 260 (indicated by arrow A in FIG. 10. When this embodiment of needle 20 is fully inserted through the sample, rotation about its longitudinal axis without substantial linear advancement or withdrawal allows tooth 260 to performs the cutting or weakening discussed previously. It will be understood that finger 52 can be cut at approximately a meeting point between it and the main portion of member 22, as shown, or at a point between such meeting points. In the latter case, two teeth 260 can be formed by bending finger 52 inward on both sides of the cut.

As previously noted, needle 20 in its most basic form does not require the complicated firing mechanisms in other devices. While such mechanisms could be used with part or all of embodiments of needle 20, the fact that needle 20 can be used without such fast-propulsion mechanisms and thus is simpler to manufacture and use is an advantage. The use of needle 20 via hand insertion through tissue to be sampled, that is, slower insertion than that performed by spring-loaded or similar biopsy needle insertion devices, is believed to be a more effective use of needle 20. The present embodiments allow for more sensitive placement by the user and avoid errors resulting from over-shooting of a needle and damage to sample tissue or surrounding tissue through sudden, fast forward propulsion.

It will be noted that features shown in particular drawing(s) or disclosed with respect to particular embodiment(s) may be included in other embodiments or with respect to other drawings.

While the disclosure has been illustrated and described in detail in the drawings and foregoing description, the same is to be considered as illustrative and not restrictive in character, it being understood that only certain specific embodiments have been shown and that all changes and modifications that come within the spirit of the disclosure are desired to be protected.

What is claimed is:

1. A biopsy needle, comprising:
   an elongated tubular member adapted for insertion into a patient to obtain a tissue sample, said tubular member having a distal portion having a distal end, the distal portion defined by a tubular wall having an outer surface with an outer diameter, said tubular member having a central longitudinal lumen along a longitudinal axis through said distal portion and said distal end,
wherein said distal portion includes a notch extending distally and radially inward a first distance into the lumen of the tubular member to separate a finger from a remainder of the tubular member, wherein said finger includes a first portion having a first external surface and a second portion having a second external surface, wherein said first portion of said finger is proximal of said second portion of said finger, wherein said first external surface of said first portion is angled axially inward toward said longitudinal axis with respect to said second external surface of said second portion of said finger, wherein said first portion extends into said notch a second distance less than the first distance to form at least one tooth with a side sharp edge extending into said lumen, wherein said at least one tooth has a thickness profile that tapers to a sharp tip of said side sharp edge, said thickness profile of said tooth defined by a cut through the tubular wall to form said notch, said cut made at an oblique angle with respect to the longitudinal axis, the first and second distances measured perpendicular to the longitudinal axis, wherein when a tissue sample enters the lumen it contacts the at least one tooth and extends beyond the finger within the lumen, and
wherein said tubular member is configured so that rotation around said axis causes the tooth to separate at least a portion of tissue within said lumen from adjacent tissue.

2. The needle of claim 1, wherein said finger connects to the rest of said tubular member at two locations.

3. The needle of claim 1, wherein said first portion disconnected from the rest of said tubular member.

4. The needle of claim 1, further comprising a slot through said inner and outer surfaces of said tubular member and adapted to permit a tissue sample to exit said tubular member, said slot being proximal of said notch.

5. The needle of claim 1, wherein said finger is adapted to elastically flex outward away from said lumen by pressure from a tissue sample moving through said lumen when said tubular member is forced through tissue.

6. The needle of claim 1, wherein said tubular member has a leading edge, and wherein said tooth and sharp edge are in a portion of said tubular member diametrically opposite to said leading edge.

7. The needle of claim 1, wherein said tubular member has a leading edge, and wherein said tooth and sharp edge are in a portion of said tubular member lateral of said leading edge.

8. The needle of claim 1, further comprising a longitudinal protrusion fixed to said tubular member within said lumen.

9. The needle of claim 8, wherein said protrusion substantially faces said notch.

10. The needle of claim 8, further comprising a mandrel having a first portion movable through said lumen, said first portion having a surface configured to face said tooth so that said mandrel can move without substantial interference with said tooth.

11. The needle of claim 10, wherein said surface of said mandrel includes a surface that is at least one of flat and longitudinally grooved.

12. A method of taking a biopsy using the needle of claim 1, comprising:
   inserting said tubular member into tissue of a patient that is to be sampled, so that tissue to be sampled enters said lumen to a position proximal of said finger;
   rotating said tubular member with respect to the tissue, said rotating reducing the area of connection between the tissue within said lumen and adjoining tissue;
   withdrawing said tubular member from said patient, said at least one tooth blocking the tissue proximal of said finger within said lumen from exiting said needle.

13. The method of claim 12, wherein said rotating causes said at least one tooth to cut a profile through tissue within said lumen.

14. The method of claim 12, wherein said rotating generates twisting strain between tissue within said lumen and adjoining tissue, resulting in a separation between tissue within said lumen and adjoining tissue or weakening of the join between tissue within said lumen and adjoining tissue.

15. The needle of claim 1, wherein the notch is between spaced-apart facing first and second surfaces, the first surface on the finger and the second surface on the remainder of the tubular member.

16. The needle of claim 1, further comprising a handle that is one of fixed and rotatable with respect to the tubular member.

17. The needle of claim 1, the second external surface of the second portion of the finger is concentric with the outer surface of the distal portion.

18. The needle of claim 17, wherein the second portion of said finger forms an arch with two separated ends each fixed to the remainder of the tubular member when the first of said finger is bent down into said lumen.

19. The needle of claim 1, wherein the notch extends approximately half-way through the outer diameter into the lumen of the tubular member.

20. The needle of claim 1, wherein said tooth of said first portion is laterally flanked by and extends axially inward from a first segment and a second segment of said second portion of said finger.

* * * * *